(12) United States Patent
Negishi

(10) Patent No.: US 7,798,959 B2
(45) Date of Patent: Sep. 21, 2010

(54) ENDOSCOPE LIGHT SOURCE UNIT WITH LIGHT QUANTITY CONTROL

(75) Inventor: Kiyoshi Negishi, Saitama (JP)

(73) Assignee: Hoya Corporation, Tokyo (JP)

( * ) Notice: Subject to any disclaimer, the term of this patent is extended or adjusted under 35 U.S.C. 154(b) by 1112 days.

(21) Appl. No.: 11/428,596

(22) Filed: Jul. 5, 2006

(65) Prior Publication Data

US 2007/0010712 A1 Jan. 11, 2007

(30) Foreign Application Priority Data

Jul. 5, 2005 (JP) ............................. 2005-196524
Jul. 5, 2005 (JP) ............................. 2005-196525

(51) Int. Cl.
*A61B 1/06* (2006.01)

(52) U.S. Cl. ........................ 600/181; 600/180; 362/574

(58) Field of Classification Search ................. 600/178, 600/180, 181, 118; 362/574

See application file for complete search history.

(56) References Cited

U.S. PATENT DOCUMENTS

| | | | | | |
|---|---|---|---|---|---|
| 2,063,222 | A | * | 12/1936 | Beau ........................... | 356/70 |
| 3,848,985 | A | * | 11/1974 | Bennett ....................... | 396/207 |
| 4,249,807 | A | * | 2/1981 | Webster et al. .............. | 396/548 |
| 4,322,129 | A | * | 3/1982 | Takahashi et al. ........... | 359/230 |
| 4,618,260 | A | * | 10/1986 | Okubo ......................... | 356/331 |
| 4,901,144 | A | * | 2/1990 | English et al. ................ | 348/69 |
| 5,006,965 | A | * | 4/1991 | Jones .......................... | 362/552 |
| 5,515,119 | A | * | 5/1996 | Murdock et al. ............. | 352/131 |
| 5,642,456 | A | * | 6/1997 | Baker et al. ................. | 385/140 |
| 5,896,224 | A | * | 4/1999 | Kapitza ....................... | 359/389 |
| 5,971,919 | A | * | 10/1999 | Davis .......................... | 600/180 |
| 6,322,497 | B1 | | 11/2001 | Takahashi | |
| 6,724,418 | B1 | * | 4/2004 | Takahashi .................... | 348/65 |
| 7,018,331 | B2 | * | 3/2006 | Chang et al. ................. | 600/182 |
| 7,029,437 | B2 | * | 4/2006 | Kobayashi ................... | 600/180 |

FOREIGN PATENT DOCUMENTS

| | | |
|---|---|---|
| JP | 2003-305008 | 10/2003 |
| JP | 2006-006803 | 1/2006 |

(Continued)

OTHER PUBLICATIONS

U.S. Appl. No. 11/428,673 to Negishi, filed Jul. 5, 2006.

(Continued)

*Primary Examiner*—John P Leubecker
(74) *Attorney, Agent, or Firm*—Greenblum & Bernstein P.L.C.

(57) ABSTRACT

An endoscope light source unit for making illumination light incident on an incident end face of a light guide connected thereto, includes an aperture device having aperture openings of different opening ratios, for selectively positioning one of the aperture openings between the incident end face of the light guide and the light source; a reading device for reading information on an illumination light quantity limit from a memory provided in a scope connected to the endoscope light source unit; and a controller for selecting an opening ratio of the aperture device in accordance with the information on the illumination light quantity limit read by the reading device, wherein the controller controls the aperture device so as not to position any of the aperture openings, which have an opening ratio higher than the selected opening ratio, between the incident end face of the light guide and the light source.

20 Claims, 8 Drawing Sheets

FOREIGN PATENT DOCUMENTS

| | | |
|---|---|---|
| JP | 2006-006832 | 1/2006 |
| JP | 2006-051151 | 2/2006 |
| JP | 2006-136519 | 6/2006 |
| JP | 2006-149933 | 6/2006 |
| JP | 2006-149939 | 6/2006 |

OTHER PUBLICATIONS

U.S. Appl. No. 11/428,752 to Negishi, filed Jul. 5, 2006.
English language Abstract of JP 2003-305008, Oct. 28, 2003.
English language Abstract of JP 2006-6803, Jan. 12, 2006.
English language Abstract of JP 2006-6832, Jan. 12, 2006.
English language Abstract of JP 2006-051151, Feb. 23, 2006.

* cited by examiner

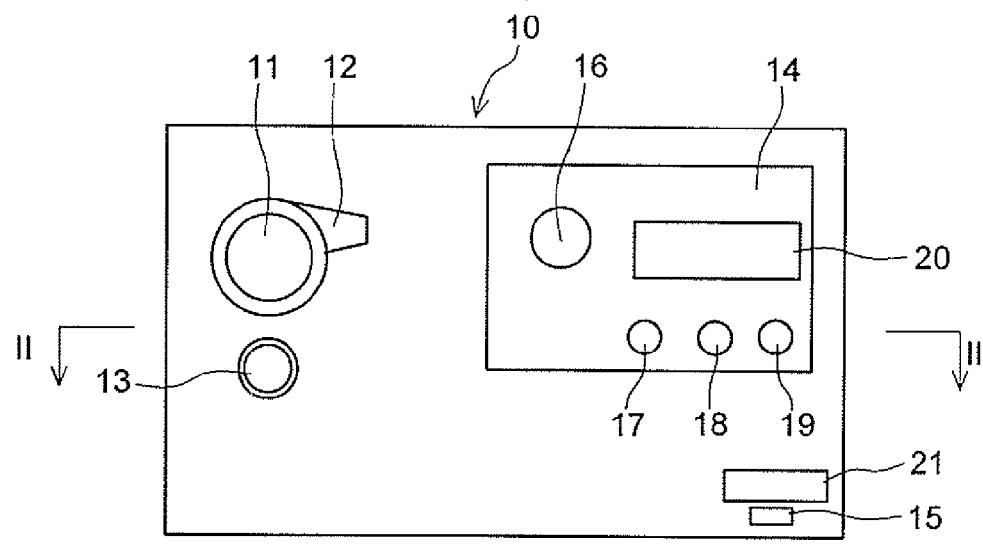
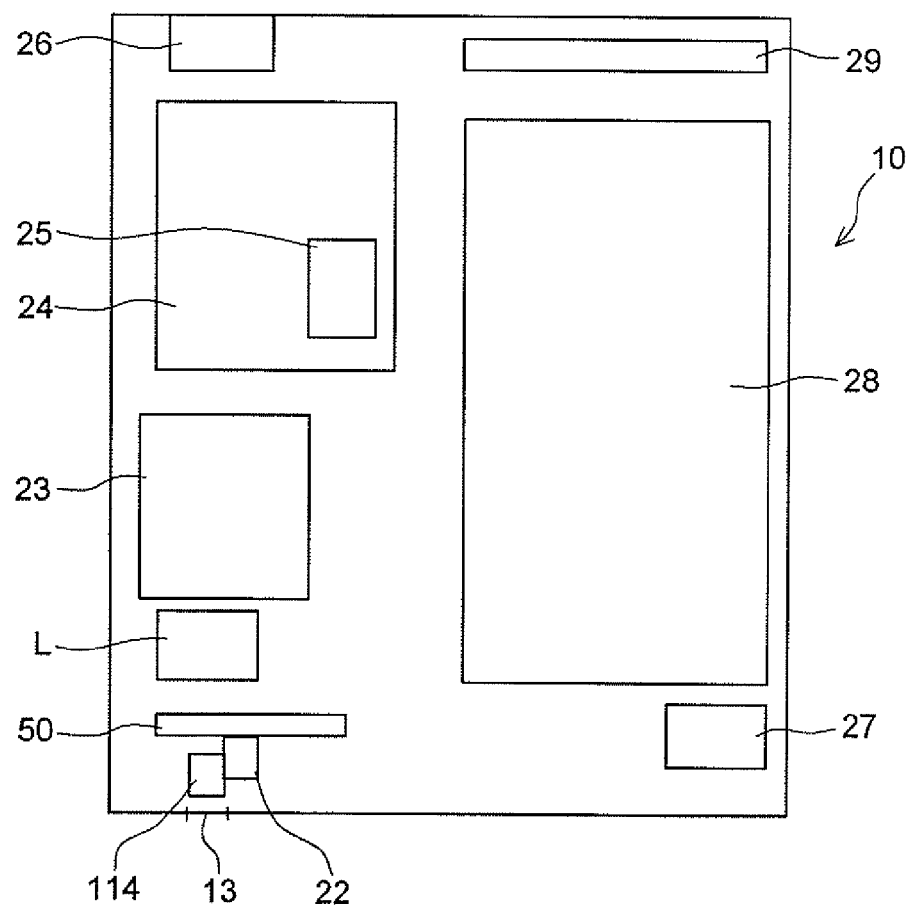

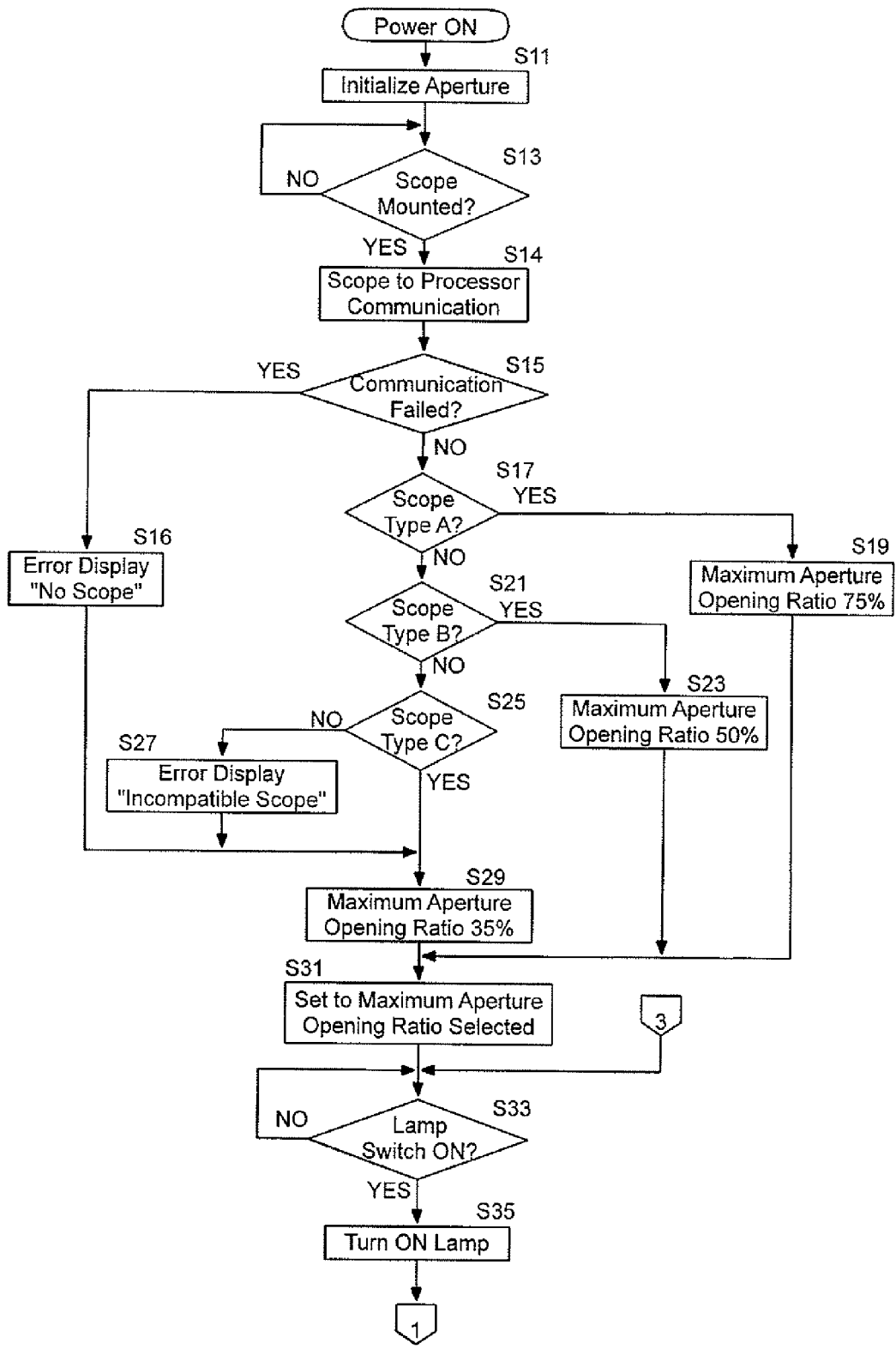

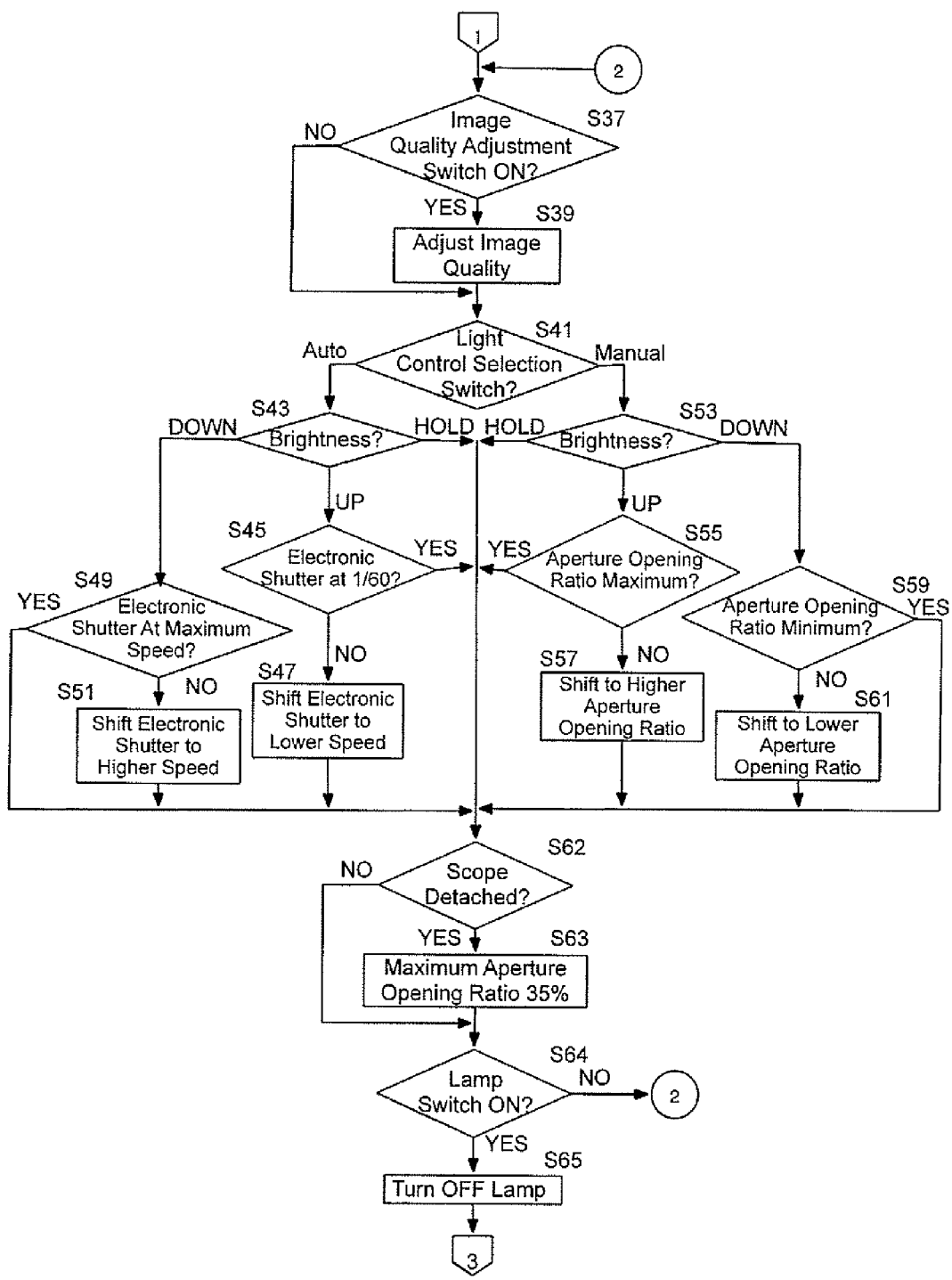

ENDOSCOPE LIGHT SOURCE UNIT WITH LIGHT QUANTITY CONTROL

BACKGROUND OF THE INVENTION

1. Field of the Invention

The present invention relates to an endoscope light source unit suitable for an endoscope or an electronic endoscope, etc.

2. Description of the Related Art

Recent electronic endoscope systems have a processor with a built-in light source unit, to which an electronic scope having an electronic camera mounted on the distal end thereof or a fiber scope for conducting observation only through optical members is connected for use. In particular, electronic scopes have been provided for use with a wide variety of thicknesses and functions suited to different locations of observation. Processors connectable with various types of electronic scopes and fiber scopes must also have light source units that are compatible with such various electronic scopes and fiber scopes. For this reason, conventional light source units have been constructed so as to supply necessary amounts of light to electronic scopes that require a maximum light quantity.

Such light source units are configured such that illumination light emitted from a high-intensity lamp is condensed by a condenser lens and made incident on the incident end face of a scope light guide, typically an optical fiber bundle. Since the necessary quantity of illumination light varies with the type of electronic scope and with the observation location, the light source units are equipped with an aperture device for adjusting the amount of light mechanically. Among known aperture devices is one that includes a diaphragm which is composed of a partly-notched portion and an arm portion integrated with the partly-notched portion, having such a size that all the light from a light source lamp can be blocked; and a motor mechanically connected to an end of the arm portion. The motor is rotated to turn the diaphragm about the top of the arm portion, thereby adjusting the illumination quantity (see Japanese Patent Laid-Open Publication No. 2003-305008). Moreover, a light shielding plate may be provided with a plurality of aperture openings having different opening ratios or transmittances so as to form a rotary aperture plate which regulates the amount of light incident on the incident end face of a light guide by putting one of the aperture openings selectively between a light source unit and the incident end face of the scope light guide (i.e., into the illumination optical path).

Such a light source unit uses high-intensity lamps such as a metal halide lamp or a xenon lamp. The higher intensities the lamps have, the more heat components the illumination light contains. Consequently, depending on the type of scope, the light source unit may be excessive in intensity, and also may heat up the ends of the scopes due to the heat components of the illumination light unless the quantity of the light source unit is turned down.

Some light source units adjust picture brightness without activating aperture devices but by adjusting the electronic shutter speed. In such a light source unit, pictures (images) of appropriate brightness can be obtained by increasing the electronic shutter speed, whereas an excessively high quantity of the illumination light can heat up the end of the light guides, i.e., the distal end of the scope. The same problem can also occur in the case of manual brightness adjustment.

Moreover, conventional light sources can be turned on even without a scope connect thereto, which has sometimes caused a problem since illumination light of maximum quantity can leak from light guide connection sockets.

SUMMARY OF THE INVENTION

The present invention has been achieved in view of the foregoing problems of the prior art. The present invention provides an endoscope light source unit which can regulate the maximum amount of illumination light in accordance with the amount of illumination light allowable in a scope connected thereto.

The present invention provides an endoscope light source unit which allows safe use of a scope even if the amount of illumination light of the scope is unknown, and can reduce the effect of leakage of illumination light when no scope is connect to the endoscope light source unit.

According to an aspect of the present invention, an endoscope light source unit is provided for making illumination light from a light source incident on an incident end face of a light guide connected thereto, the endoscope light source unit including an aperture device having a plurality of aperture openings of different opening ratios, for selectively positioning one of the aperture openings between the incident end face of the light guide and the light source; a reading device for reading information on an illumination light quantity limit from a memory provided in a scope which is connected to the endoscope light source unit; and a controller for selecting an opening ratio of the aperture device in accordance with the information on the illumination light quantity limit read by the reading device, wherein the controller controls the aperture device so as not to position any of the aperture openings, which have an opening ratio higher than the selected opening ratio, between the incident end face of the light guide and the light source.

It is desirable for the information on the illumination light quantity limit to include identification information measured and set in advance in terms of light quantity and temperature.

It is desirable for the aperture device to include a disc and drive device for rotatably driving the disc, the aperture openings of different aperture ratios being formed in the disc at equi-angular intervals thereon about a center of rotation thereof. The controller controls the drive device so that one of the aperture openings intersects an illumination optical path between the incident end face of the light guide and the light source.

It is desirable for each of the aperture openings to include a plurality of small holes formed in the disc at predetermined intervals; and for the opening ratios to be determined by differing densities of the small holes.

It is desirable for each of the aperture openings to include a plurality of small holes formed in the disc at predetermined intervals; and for the opening ratios to be determined by differing diameters of the small holes.

It is desirable for each of the aperture openings to include a plurality of small holes formed in the disc at predetermined intervals; and the opening ratios to be determined by differing densities and diameters of the small holes.

It is desirable for the small holes to be circular in shape.

It is desirable for the small holes to be polygonal in shape.

It is desirable for the endoscope light source unit to include an initial-position detection sensor which detects a initial position of the disc, wherein one of the plurality of aperture openings which have a smaller opening ratio than a maximum opening ratio intersects the illumination optical path between the incident end face of the light guide and the light source at the initial position. The maximum opening ratio of the aperture openings of the disc is an opening ratio which prevents an excessively large quantity of the illumination light from passing through the disc to provide a safe light quantity for any electronic scope which is connectable to the endoscope light source unit. It is desirable for the controller to drive the drive device so as to rotate the disc so that the one of the plurality of aperture openings intersects the illumination optical path between the incident end face of the light guide and the light source.

It is desirable for an aperture opening having the maximum opening ratio or the one of the aperture openings which is smaller than the maximum opening ratio, to intersect the illumination optical path between the incident end face of the light guide and the light source at the initial position.

In an embodiment, an endoscope light source unit is provided for making illumination light from a light source incident on an incident end face of a light guide connected thereto, the endoscope light source unit including an aperture device having a plurality of aperture openings of different opening ratios, for selectively positioning one of the aperture openings between the incident end face of the light guide and the light source; a reading device for reading information on an illumination light quantity limit from a memory provided in a scope which is connected to the endoscope light source unit; and a controller for selecting an opening ratio of the aperture device in accordance with the information read by the reading device, wherein the controller controls the aperture device so as not to position any of the aperture openings, which have an opening ratio higher than the selected opening ratio, between the incident end face of the light guide and the light source. The controller selects an opening ratio lower than a maximum opening ratio of the aperture device in the case where the reading device fails to read the information on the illumination light quantity limit from the memory.

It is desirable for the controller to select an opening ratio which is lower than the maximum opening ratio of the aperture device in the case where the controller determines via the reading device that no scope is connected to the endoscope light source unit.

It is desirable for the controller to select an opening ratio which is lower than the maximum opening ratio of the aperture device in the case where the controller determines via the reading device that a fiber scope is connected to the endoscope light source unit.

It is desirable for the information on the illumination light quantity limit to include identification information measured and set in advance in terms of light quantity and temperature.

It is desirable for the aperture device to include a disc and drive device for rotatably driving the disc, the aperture openings of different aperture ratios being formed in the disc at equi-angular intervals thereon about a center of rotation thereof. The controller drives the drive device so that one of the aperture openings intersects an illumination optical path between the incident end face of the light guide and the light source.

It is desirable for the endoscope light source unit to include an initial-position detection sensor which detects a initial position of the disc, wherein one of the plurality of aperture openings which have a smaller opening ratio than a maximum opening ratio intersects the illumination optical path between the incident end face of the light guide and the light source at the initial position. The maximum opening ratio of the aperture openings of the disc is an opening ratio which prevents an excessively large quantity of the illumination light from passing through the disc to provide a safe light quantity for any electronic scope which is connectable to the endoscope light source unit. It is desirable for the controller to drive the drive device so as to rotate the disc so that the one of the plurality of aperture openings intersects the illumination optical path between the incident end face of the light guide and the light source.

It is desirable for an aperture opening having the maximum opening ratio or the one of the aperture openings which is smaller than the maximum opening ratio, to intersect the illumination optical path between the incident end face of the light guide and the light source at the initial position.

It is desirable for the endoscope light source unit to include a main switch for supplying power to the controller; and a lamp switch for turning ON the light source. When the main switch is turned ON, the controller reads the information on the illumination light quantity limit, selects an opening ratio, and drives the drive device so that an aperture opening of the aperture device having the selected opening ratio intersects the illumination optical path between the incident end face of the light guide and the light source.

It is desirable for the endoscope light source unit to include a display device for displaying a result of determination of the controller.

According to the present invention, an opening ratio or transmittance is selected in accordance with the information on the connected scope, and control is performed so that aperture openings are not set to opening ratios or transmittances higher than the selected opening ratio or transmittance. Consequently, even if the connected scope has a high maximum quantity, it is possible to prevent the scope end from rising in temperature excessively due to an excessive amount of light. Even if the connected scope has a low maximum quantity, it is possible to obtain a sufficient amount of light.

Moreover, according to the present invention, an opening ratio or transmittance lower than the maximum opening ratio or the maximum transmittance of the aperture is selected when the aperture information cannot be read out so as to avoid an excessive quantity of light being illuminated.

The present disclosure relates to subject matter contained in Japanese Patent Application Nos. 2005-196524 and 2005-196525 (both filed on Jul. 5, 2005) which are expressly incorporated herein in their entirety.

BRIEF DESCRIPTION OF THE DRAWINGS

The present invention will be discussed below in detail with reference to the accompanying drawings, in which:

FIG. 1 is a front view showing an overview of an embodiment of a processor to which an endoscope light source unit according to the present invention is applied;

FIG. 2 is an abbreviated cross sectional view taken along the II-II line of in FIG. 1, showing essential components of the processor;

FIG. 9 is a flowchart showing a second embodiment of a first half of a control operation for illumination of the processor; and FIG. 10 is a flowchart showing the second embodiment of a second half of the control operation shown in FIG. 9.

DESCRIPTION OF THE PREFERRED EMBODIMENT

Figure 3:
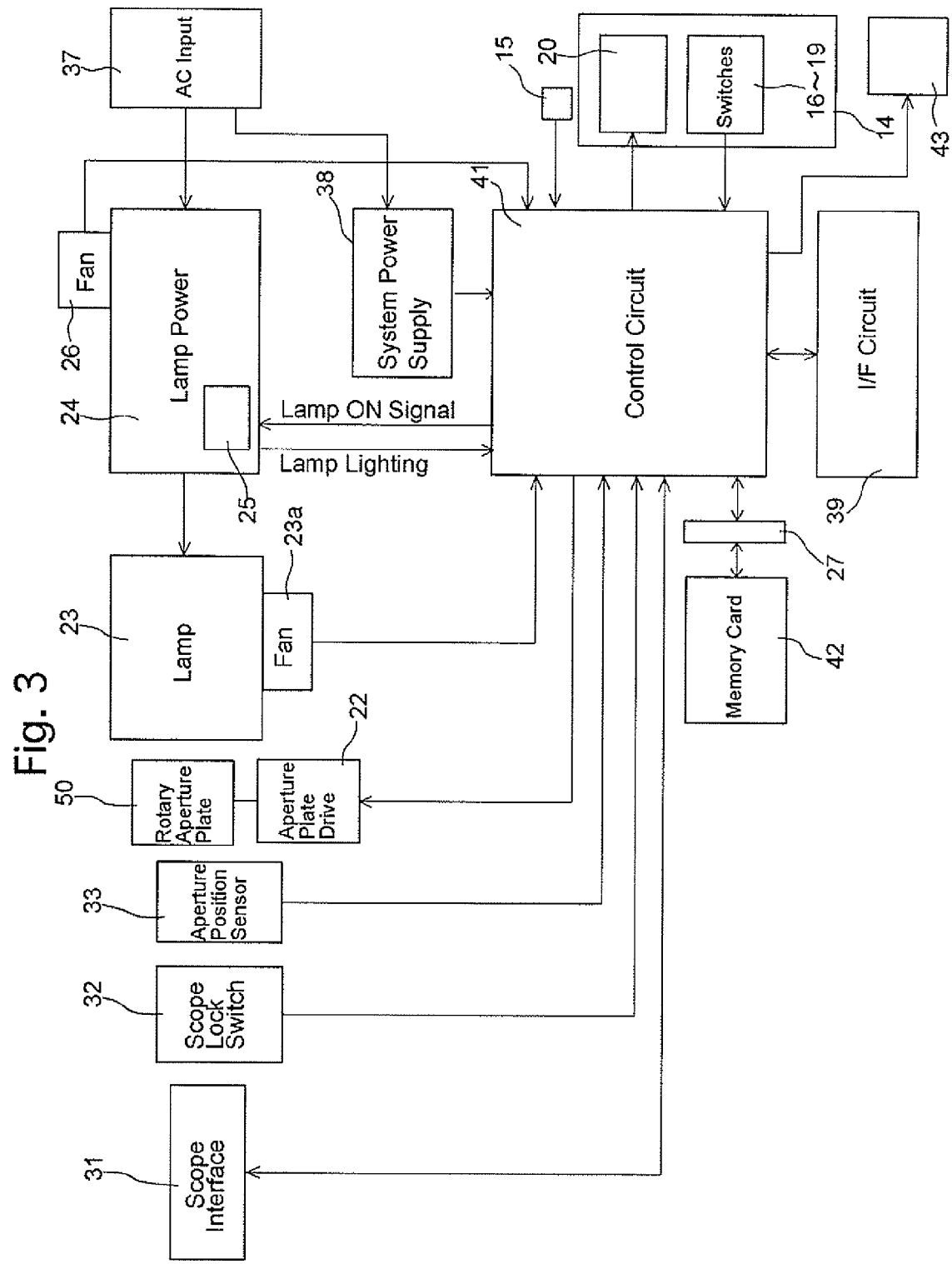
FIG. 3 is a block diagram showing essential circuits of the processor, according to the present invention.

Embodiments of the invention will be described with reference to the accompanying drawings. FIG. 1 is a front view of a processor (endoscope light source unit) 10 that contains a power supply unit to which the present invention is applied. FIG. 2 is an abbreviated cross sectional view taken along the II-II line of in FIG. 1, showing essential components of the processor 10.

The processor 10 is provided on the front thereof (as viewed in FIG. 1) with a scope socket 11 into which a connector 104 of an electronic scope 100 is to be inserted (see FIG. 4), and a scope lock lever 12 for locking the inserted connector 104 so as not to come off. The scope socket 11 establishes connection with connect pins, or the like, provided in the connector 104 of the electronic scope 100. A light guide socket 13 for the light guide connector 115 of the electronic scope 100 (or a fiber scope) to be inserted into is formed below the scope socket 11.

The processor 10 also has an operation panel 14 on the front, beside the scope socket 11. This operation panel 14 is provided with operation switches such as a lamp switch 16, an image quality adjustment switch (image quality adjustment button) 17, a light control selection switch (light control selection button) 18, a manual adjustment switch 19, and a scope information display 20. A memory card slot 21 for a removable memory card to be loaded into and a main switch 15 are also formed below the operation panel 14.

The processor 10 contains a rotary aperture plate 50 which is arranged behind the light guide socket 13. This rotary aperture plate 50 has a plurality of aperture openings having different opening ratios, which are arranged in the circumferential direction of this circular plate. An aperture plate drive motor (drive device) 22 rotationally drives so that any one of the aperture openings is opposed to an incident end face 113a of a light guide 113 which is plugged into the light guide socket 13 (see FIG. 4). A condenser lens L is arranged on the opposite side of the rotary aperture plate 50 from the incident end face 113a, with a lamp (light source) 23 provided behind the condenser lens L. As shown in FIG. 5, the light source 23 has a built-in high-intensity lamp 35. Illumination light emitted from the lamp 35 is focused by the condenser lens L so that the light beam passing through any one of the aperture openings of the rotary aperture plate 50 is incident on the incident end face 113a. The vicinity of the incident end face 113a of the light guide 113 is fixed inside a light guide sleeve 114 which is made of metal.

As shown in FIG. 2, the processor 10 also contains a lamp power supply 24 which has an igniter 25 for turning on the light source 23. A cooling fan 26 for cooling the lamp power supply 24 is formed on the rear panel of the processor 10.

In the processor 10, a memory card board 27 is arranged near the memory card slot 21. The memory card board 27 is electrically connected with the memory card loaded in the memory card slot 21, and functions as an interface circuit controls reading and writing from/to the memory card. For example, the read/write control includes reading information written in the memory card, and writing information such as image information processed by the processor 10 to the memory card. The processor 10 also contains a control board 28 on which circuits such as a control circuit (controller/reading device) 41 and an image processing circuit are mounted. The control circuit 41 controls the operations of the entire processor 10, including the control of the memory card board 27 and the aperture plate drive motor 22. The image processing circuit of the control board 28 reads stored information from an EEPROM (memory) 109 of the electronic scope 100, drives a CCD sensor (image pickup device) 105 of the electronic scope 100, processes picture signals obtained by the CCD sensor 105, and displays the processed picture signals on a monitor display 43. The picture signals processed by the control board 28 are output from a picture connector (not shown) provided on a back panel substrate 29. A predetermined picture is then displayed on the monitor display 43.

FIG. 3 shows essential components of the circuit configuration of the processor 10. A scope interface 31 is provided inside the scope socket 11. The scope interface 31 is provided with a plurality of connectors, including an information connector and the picture connector. The information connector is for reading information written in the EEPROM 109 of the electronic scope 100. The picture connector transmits a drive clock of the CCD sensor 105, and inputs picture signals output from the CCD sensor 105. Each connector is connected to respective corresponding terminals, such as those of the control circuit 41 formed on the control substrate 28.

A scope lock switch 32 is a detection switch for detecting if the scope lock lever 12 is in a locked state. The state signal of the scope lock switch 32 is input to the control circuit 41.

The aperture plate drive motor 22 for rotationally driving the rotary aperture plate 50 is driven and controlled by the control circuit 41. The rotation position of the rotary aperture plate 50 is detected by an aperture position sensor (initial-position detection sensor) 33 and the control circuit 41 receives the signal detected thereby.

The light source 23 is turned on by the igniter 25 of the lamp power supply 24 which is controlled ON/OFF by the control circuit 41. The light source 23 is also provided with a lamp cooling fan 23a. The lamp cooling fan 23a is driven and controlled by the control circuit 41. The igniter 25 for turning ON and driving the light source 23 is driven by the lamp power supply 24 which is powered by an AC input 37, typically a commercial alternating-current power.

The AC input 37 also powers a system power supply 38 which outputs a constant voltage for driving electronic circuits such as the control circuit 41. The control circuit 41 is activated to start processing when the main switch 15 is turned ON, and transmits a lamp-ON signal to the lamp power supply 24 to turn ON the light source 23 via the igniter 25 when the lamp switch 16 is turned ON.

The control circuit 41 reads aperture-related information from the EEPROM 109 of the electronic scope 100 via the scope interface 31, and selects a maximum opening ratio of the rotary aperture plate 50 for use when adjusting the amount of the illumination light. In this case, the scope interface 31 functions as reading device.

The control circuit 41 also performs image capturing processing for driving the CCD sensor 105 of the electronic scope 100 and inputs an image signal from the CCD sensor 105 via the scope interface 31. Moreover, the control circuit 41 performs a predetermined image signal process, and displays the image signal on the monitor display 43 or writes the image data thereof to the memory card 42 via the card board 27. It should be appreciated that if the control circuit 41 starts the image capturing process when the main switch 15 is turned ON, the image capturing process is usually performed by the image processing circuit which is separate from the control circuit 41.

The control circuit 41 is also connected with an input device such as a keyboard via an I/F circuit 39 so that individual information necessary for endoscopic inspection can be entered via the input device.

Figure 4:
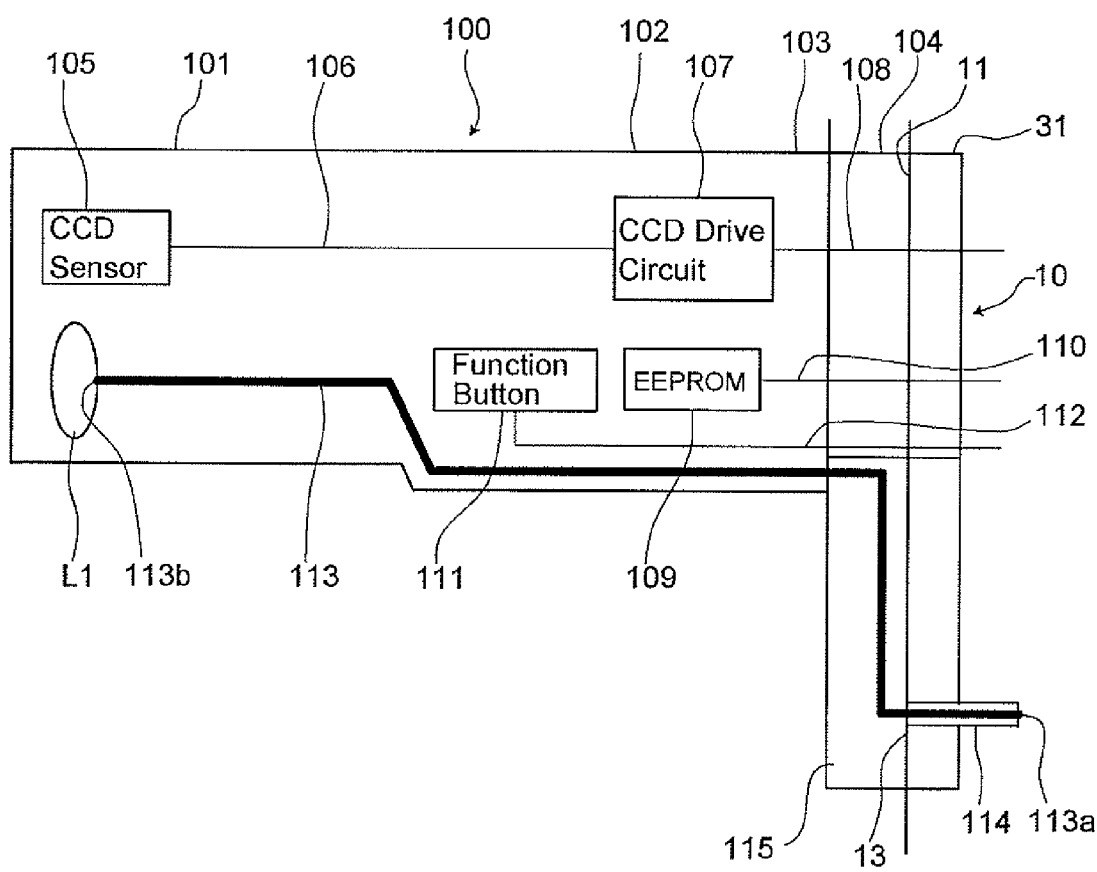
FIG. 4 is a schematic diagram of an electronic scope which is connectable to the processor, according to the present invention.
Figure 5:
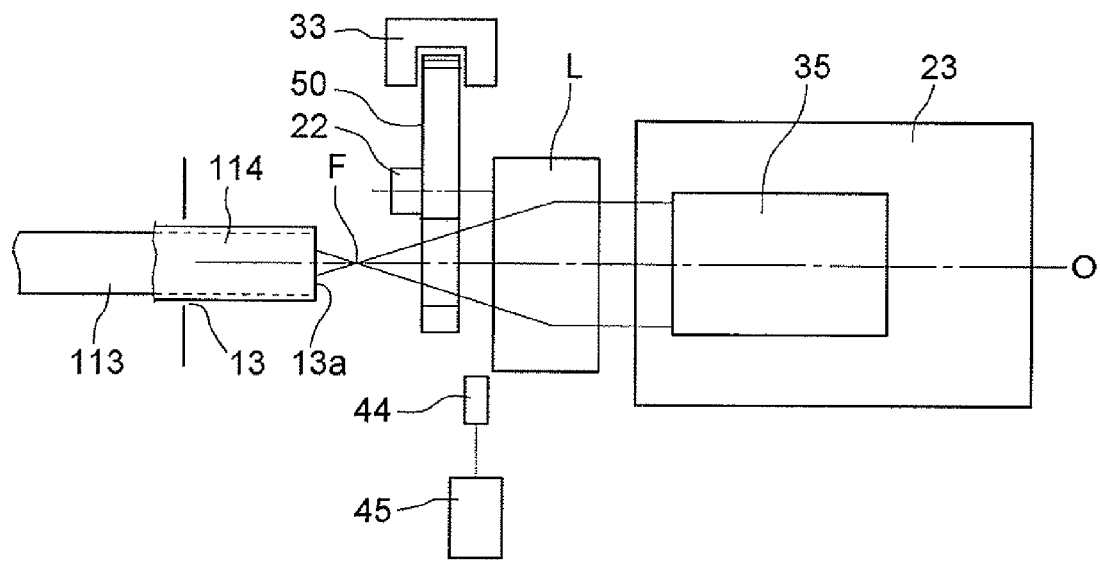
FIG. 5 is an explanatory diagram showing various components which are provided near the light source unit of the processor.

FIG. 4 is a diagram showing a schematic view of the electronic scope 10 which is connected to the processor 10. As shown in FIG. 4, the electronic scope 100 has a flexible insertion portion 101 and an operation portion 102. The connector 104 is arranged on the top of a universal tube 103 which extends from the operation portion 102. The CCD sensor 105 and a light distribution lens L1 for light illumination are arranged at the distal end of the flexible insertion portion 101. The CCD sensor 105 is connected to a CCD drive circuit 107 formed in the operation portion 102, via a picture line 106 which is laid through the insertion portion 101. The CCD drive circuit 107 is also connected with a picture transmission line that is laid through the operation portion 102 and the universal tube 103. The picture transmission line 108 is connected to signal pins formed in the connector 104. The EEPROM 109, containing such information as the type of the electronic scope 100, is provided in the operation portion 102. A read/write line 110, which is connected with input and output terminals of the EEPROM 109, is connected to signal pins of the connector 104. The operation portion 102 also includes a function button 111 for making operations of taking a moving image, and photographing a still image, etc. A switch line 112 in connection with the contacts of the function button 111 is connected to signal pins in the connector 104.

The exit end 113b of the light guide 113 is placed behind the light distribution lens L1. The light guide 113 is introduced through the insertion portion 101, the operation portion 102, the universal tube 103, and the connector 104, and is inserted and fixed inside the light guide sleeve 114 which protrudes out of the connector 104. The incident end face 113a of the light guide 113 is opposed to the open end of the light guide sleeve 114.

The EEPROM 109 provided in the electronic scope 100 contains at least the information for identifying the type of scope, i.e., an illumination light quantity limit of the scope. In this embodiment, scope types are classified into a plurality of groups stepwise depending on the illumination light quantity limit, i.e., the maximum amounts of light allowed for the light guide 113 to emit. In the present embodiment, the scope types are classified into three groups, i.e., type A, type B, and type C, in descending order of the amount of light.

FIG. 5 is a diagram showing various components which are provided near the light source 23 of the processor 10. As shown in FIG. 5, the rotary aperture plate 50 is interposed between the incident end face 113a of the light guide sleeve 114 (light guide 113), which is inserted from the light guide socket 13, and the condenser lens L which is provided in front of the light source 23. The incident end face 113a is normally placed orthogonal to the optical axis O of the condenser lens L, away from the focal point F of the condenser lens L. The substantially parallel illumination light emitted from the lamp 35 is focused at the focal point F by the condenser lens L, so that the light beam passing through the rotary aperture plate 50 gathers at the focal point F and thereafter diverges so as to be incident on the incident end face 113a. The illumination light beam entering from the incident end face 113a is guided through the light guide 113, and emitted from the exit end 113b (see FIG. 4) of the light guide 113 provided at the distal end of the insertion portion 101. The emitted light then passes through the light distribution lens L1 for distribution (FIG. 4) so as to illuminate an object.

Figure 6:
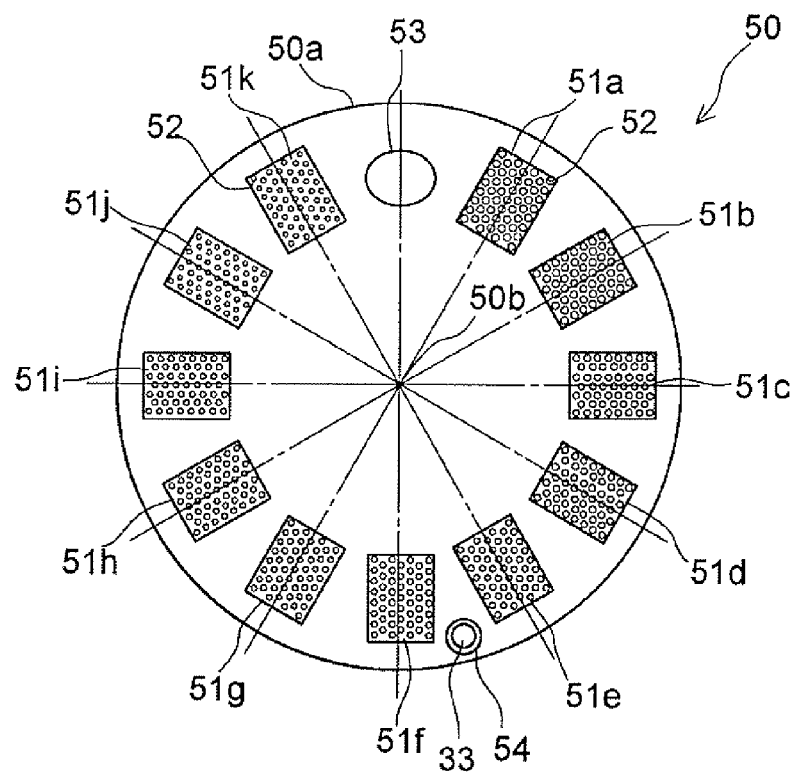
FIG. 6 is a front view of the rotary aperture plate of the aperture device of the light source unit, according to the present invention.

FIG. 6 is a front view of the rotary aperture plate 50 of the aperture device for the light source 23. As shown in FIG. 6, the rotary aperture plate 50 is made of an aluminum disc 50a. The disc 50a is fixed to a rotary shaft of the aperture plate drive motor 22 centered at the center of rotation 50b. The disc 50a has twelve openings which are formed at predetermined intervals circumferentially about the center of rotation 50b (at 30 degree intervals). In the illustrated embodiment, the disc 50a is provided with first to eleventh aperture openings 51a to 51k, and an auxiliary lamp opening 53. The first aperture opening 51a has an opening ratio of 70%. The opening ratios are determined to decrease stepwise, clockwise from the first aperture opening 51a. The second to eleventh aperture openings 51b to 51k have opening ratios of 50%, 35%, 25%, 18%, 13%, 9%, 7%, 5%, 3.5%, and 2%, respectively. The auxiliary lamp opening 53 has an opening ratio of 100%.

In the electronic scope 100 of the illustrated embodiment, type A corresponds to the amount of light when the aperture opening 51a having a maximum opening ratio of 75% is set, type B corresponds to the amount of light when the aperture opening 51b having a maximum opening ratio of 50% is set, and type C corresponds to the amount of light when the aperture opening 51c having a maximum opening ratio of 35% is set.

In the illustrated embodiment, the first to eleventh aperture openings 51a to 51k have a large number of small holes 52 which are formed at a predetermined spacing in each opening area. The illumination light is either passed through these small holes 52 or blocked by the surface of the disc 50a where the small holes 52 are not formed.

In an embodiment, different opening ratios are achieved by modifying the density (spacing) of the small holes 52 of first to eleventh aperture openings 51a to 51k. Alternatively, the density (spacing) can be maintained constant and the diameters of the small holes 52 of the first to eleventh aperture openings 51a to 51k can be modified. Alternatively, both the density (spacing) and the diameter of the small holes 52 of the first to eleventh aperture openings 51a to 51k can be modified. The small holes 52 can have any shape. Each the first to eleventh aperture openings 51a to 51k may be provided with a mixture of small holes of various shapes, or may have small holes of respective different shapes. Although circular small holes are easy to form and to modify in diameter, polygonal and other shapes may also be adopted. Polygonal shapes can easily provide higher opening ratios than with circular shapes.

The rotary aperture plate 50 is driven stepwise by the aperture plate drive motor 22. It is desirable for the aperture plate drive motor 22 to be a stepping motor. In the illustrated embodiment, a stepping motor having a step angle of 0.75 degrees is used. Namely, when the aperture plate drive motor 22 rotates by 40 steps, the rotary aperture plate 50 is rotated by 30 degrees, i.e., by one aperture opening.

The rotary aperture plate 50 has an aperture position hole 54 for detecting an initial position of rotation thereof. The aperture position sensor 33 (FIG. 5) is arranged so as to detect this aperture position hole 54 when the rotary aperture plate 50 is in the initial position of rotation. In the illustrated embodiment, the aperture position hole 54 is provided in between the aperture openings 51e and 51f. Accordingly, the initial position of the rotary aperture plate 50 is determined at a rotational position such that the aperture opening 51c is positioned in the illumination optical path; the aperture opening 51c having a maximum opening ration of 35% which is deemed as being a safe opening ratio, i.e., an opening ratio which prevents an excessively large quantity of the illumination light from passing therethrough, for any electronic scope which can be mounted to the processor 10.

The aperture position sensor 33 can be a photo coupler, wherein the aperture position hole 54 opens the optical path of the photo coupler when the rotary aperture plate 50 is in the initial position; the disc 50*a* otherwise blocks the optical path of the photo coupler. In the present embodiment, the initial position refers to the state where the third aperture opening 51*c* enters (intersects) the illumination optical path.

Note that the initial position of the rotary aperture plate 50 can be alternatively be determined at a rotational position such that one of the aperture openings 51*d* through 51*k*, which have a lower opening ratio than the aperture opening 51*c*, is positioned in the illumination optical path. Accordingly, the rotary aperture plate 50 is rotated from the initial position at one of the aperture openings 51*d* through 51*k* until the aperture opening 51*c* is positioned in the illumination optical path.

As shown in FIG. 5, the processor 10 has an auxiliary light 44 that comes into operation when the lamp 35 of the light source 23 goes out due to some reason. When the control circuit 41 detects that the lamp 35 has gone out, the control circuit 41 activates an auxiliary light drive mechanism 45 to put the auxiliary light 44 into the illumination optical path and turn the auxiliary light ON. The control circuit 41 rotates the rotary aperture plate 50 so that the auxiliary lamp opening 53 enters (intersects) the illumination optical path.

Figure 7:
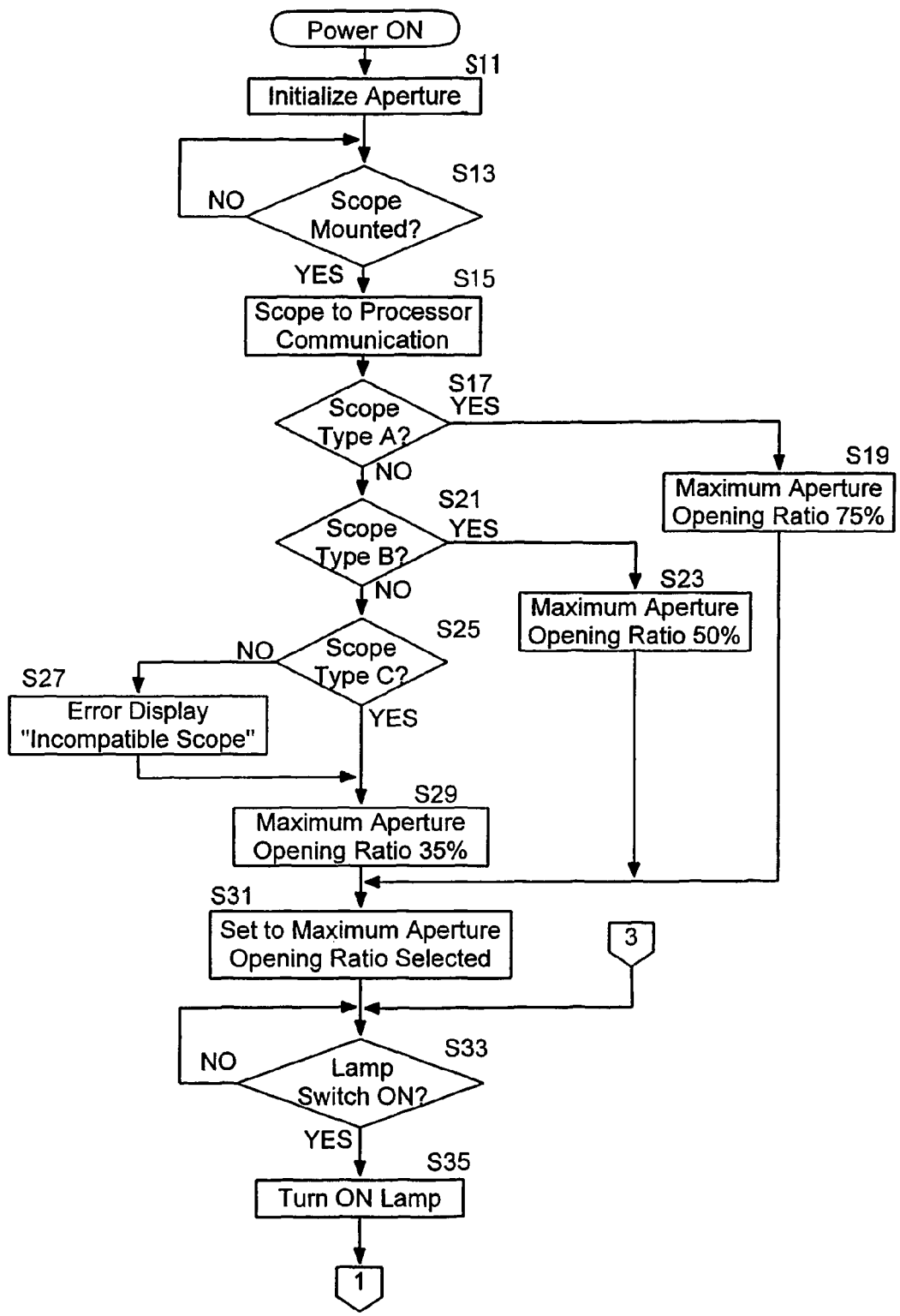
FIG. 7 is a flowchart showing a first embodiment of a first half of a control operation for illumination of the processor.
Figure 8:
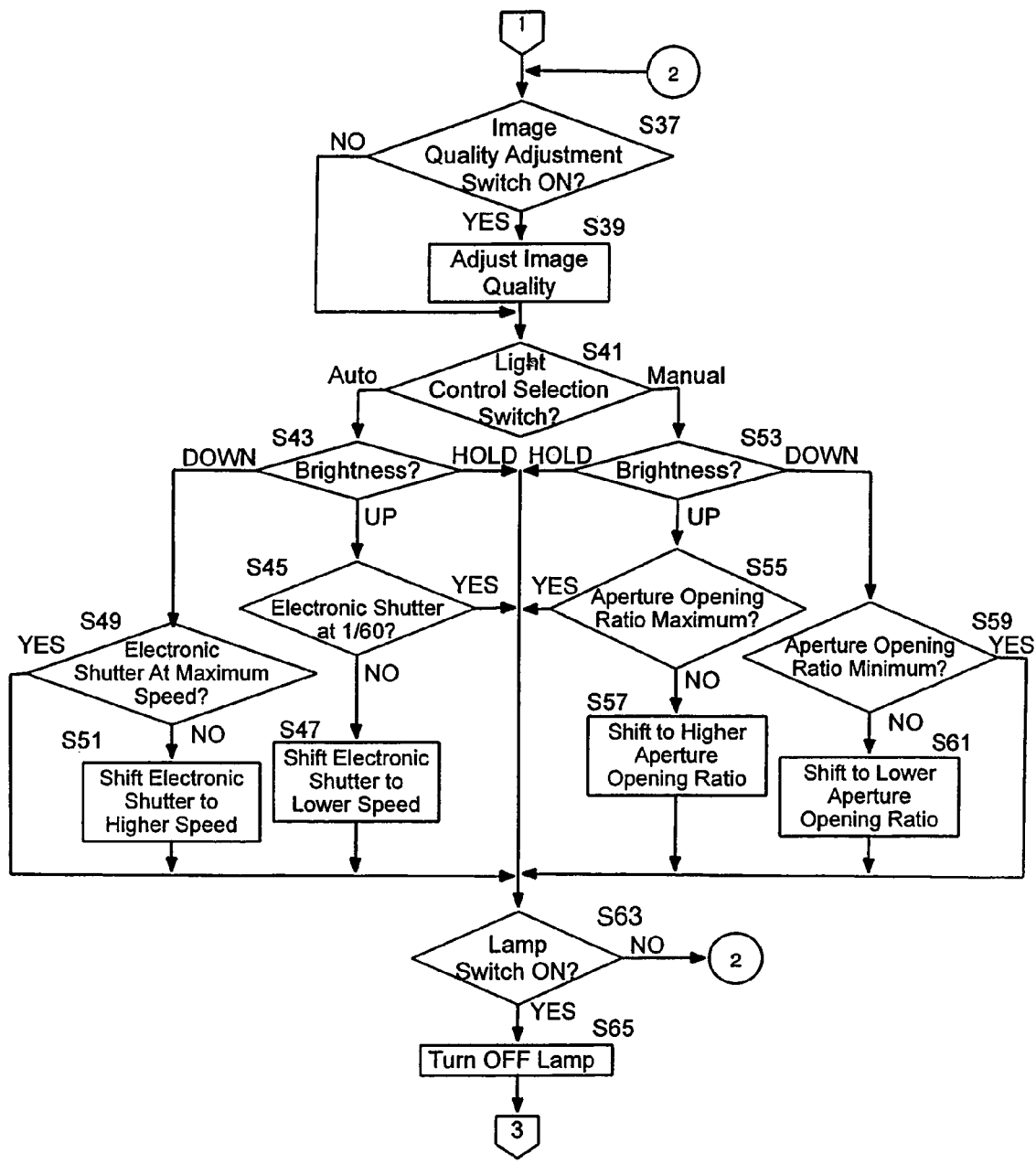
FIG. 8 is a flowchart showing the first embodiment of a second half of the control operation shown in FIG. 7.

The operation of the electronic endoscope system will be described with reference to the flowchart of the power-ON process shown in FIGS. 7 and 8. The power-ON process concerns the operation of the control circuit 41. The control circuit 41 enters this power-ON process when the main switch 15 is turned ON.

Upon entering the power-ON process, the control circuit 41 first initializes the state of the rotary aperture plate 50 (step S11). In the present embodiment, the initialization refers to rotating the rotary aperture plate 50 so that the third aperture opening 51*c* having an opening ratio of 35% enters into (intersects) the illumination optical path.

Thereafter, the control circuit 41 checks if an scope is mounted (step S13). In this embodiment, it is determined a scope is mounted if the scope lock switch 32 is ON. If a scope is mounted (step S13, YES), the mounted scope and the processor perform scope-to-processor communication so as to input scope information (step S15). The scope information includes at least information concerning the amount of illumination light, i.e., one of scope types A to C in the illustrated embodiment.

Based on the input scope information, the control circuit 41 checks whether the scope is a scope type A (step S17), scope type B (step S21), or scope type C (step S25).

In the case of a scope type A (S17, YES), the control circuit 41 selects a maximum aperture opening ratio of 75% (step S19). In the case of a scope type B (step S17, NO; step S21, YES), the control circuit 41 selects a maximum aperture opening ratio of 50% (step S23). In the case of a scope type C (step S17, NO; step S21, NO; step S25, YES), the control circuit 41 selects a maximum aperture opening ratio of 35% (step S29). If the mounted scope is none of scope types A, B, and C (step S17, NO; step S21, NO; step S25, NO), the control circuit 41 displays "incompatible scope" on the scope information display unit 20 or the monitor display 43 (step S27), and selects a maximum opening ratio of 35% (step S29). The maximum opening ratio selected here is used as the upper limit of the opening ratios in automatic light control processing and manual light control processing so that opening ratios higher than the selected one will not be set. This regulation precludes heat generation caused by excessive illumination light.

The control circuit 41 rotates the rotary aperture plate 50 stepwise so that one of the first to eleventh aperture openings 51*a* to 51*k* corresponding to the maximum aperture opening ratio selected at step S19, S23, or S29 is set (step S31). After one of the first to eleventh aperture openings 51*a* to 51*k* corresponding to the maximum aperture opening ratio selected is set, the control circuit 41 checks whether or not the lamp switch 16 is operated when the lamp 35 is OFF (step S33). The control circuit 41 repeats checking while the lamp switch 16 is not operated (step S33, NO; step S33). It should be noted that the lamp switch 16 according to the illustrated embodiment is a momentary switch. The control circuit 41 turns ON the lamp 35 if the lamp switch 16 is operated when the lamp 35 is OFF, and turns OFF the lamp 35 if the lamp switch 16 is operated while the lamp 35 is ON.

When the lamp switch 16 is operated (step S33, YES), the control circuit 41 turns ON the lamp 35 (step S35). Thereafter, the control circuit 41 checks whether or not the image quality adjustment switch 17 is ON (step S37). If the image quality adjustment switch 17 is ON, the control circuit 41 carries out an image quality adjustment and proceeds to step S41 (step S37, YES; step S39; and step S41). If the image adjustment switch is not ON, the control circuit 41 skips the image quality adjustment and proceeds to step S41 (step S37, NO; step S41).

At step S41, the control circuit 41 checks whether automatic light control or manual light control has selected by the light control selection switch 18.

If the automatic light control is selected (step S41, AUTO), the control circuit 41 checks whether to increase, decrease, or hold the brightness based on the brightness of the object image measured by the control circuit 41 (step S43). In order to increase the brightness (step S43, UP), i.e., adjust toward an overexposure, the control circuit 41 checks whether or not the electronic shutter is set to a minimum speed of ⅛₀ seconds (step 545). If the shutter speed is already set to ⅛₀ seconds, the control circuit 41 simply proceeds to step S63 since it is impossible to slow down the shutter speed further (step S45; YES, 863). If the shutter speed is not set to ⅛₀ seconds (step S45, NO), the control circuit 41 shifts the electronic shutter to a slower speed (step S47), and proceeds to step S63.

In order to decrease the brightness (step S43, DOWN), i.e., adjust toward an underexposure, the control circuit 41 checks whether or not the electronic shutter is set to a maximum speed (step S49). If the electronic shutter is set to the maximum speed (step S49. YES), the control circuit 41 simply proceeds to step S63. If the electronic shutter is not set to the maximum speed (step S49, NO), the control circuit 41 shifts the electronic shutter to a higher speed (step S51), and proceeds to step S63.

To hold the brightness (step S43; HOLD), i.e., make no adjustment on the exposure, the control circuit 41 simply proceeds to step S63.

If the manual light control is selected (step S41, MANUAL), the control circuit 41 checks whether brightness UP, DOWN, or HOLD has selected by the manual adjustment switch 19 (step S53). It should be noted that when the manual light control is selected in the illustrated embodiment, the electronic shutter speed is fixed to ⅛₀ seconds.

If brightness UP is selected by the manual adjustment switch 19 (step S53, UP), the control circuit 41 checks whether or not the aperture opening ratio is set to a maximum value. If the aperture opening ratio is set to the maximum value (step S55, YES), the control circuit 41 simply proceeds to step S63. If the aperture opening ratio is not set to the maximum value (step S55, NO), the control circuit 41 shifts (rotates) the rotary aperture plate 50 to a higher aperture opening ratio, up to the next level (step S57), and proceeds to step S63.

If brightness DOWN is selected by the manual adjustment switch 19 (step S53, DOWN), the control circuit 41 checks whether or not the aperture opening ratio is set to a minimum value (step S59). If the aperture opening ratio is set to the minimum value (step S59, YES), the control circuit 41 simply proceeds to step S63. If the aperture opening ratio is not set to the minimum value (step S59, NO), the control circuit 41 shifts the aperture opening ratio, namely, rotates the rotary aperture plate 50 down to the next level (step 861), and proceeds to step S63.

If no selection is made by the manual adjustment switch 19 (step S53, HOLD), the control circuit 41 simply proceeds to step S63.

At step S63, the control circuit 41 checks whether or not the lamp switch 16 is operated while the lamp 35 is ON. If the lamp switch 16 is not operated (step S63, NO), the control circuit 41 returns to step S37. If the lamp switch 16 is operated (step S63, YES), the control circuit 41 turns OFF the lamp 35 (step S65), and returns to step S33.

When the main switch 15 is turned OFF, the control circuit 41 turns OFF the light source 23 and exits via an interrupt process.

As described above, according to the present invention, the amount of illumination light is regulated depending on the type of scope connected to the processor 10. Consequently, even if the amount of light of the scope connected is high, it is possible to prevent the scope end from rising in temperature excessively due to an excessive amount of light. Even if the maximum amount of light of the scope connected is low, it is possible to obtain a sufficient amount of light.

When an electronic scope or fiber scope having no information corresponding to scope types A to C is mounted, an opening ratio lower than the maximum opening ratio is selected. This eliminates the possibility of a rise in temperature due to an excessive amount of light.

A second embodiment of the present invention will be described with reference to the flowchart of an alternative power-ON process shown in FIGS. 9 and 10. In the second embodiment, the same processes as in the embodiment shown in FIGS. 7 and 8 are designated by the same step numbers, and detailed descriptions thereof are omitted.

A checking process for checking whether or not the communication with the scope failed (step S15) is carried out between steps S14 and S17. If the communication failed (step S15, YES), the control circuit 41 displays "no scope" on the scope information display unit 20 or the monitor display 43 (step S16), and sets the maximum aperture opening ratio to 35% (step S29). If the communication with scope is successful (step S15, NO), the control circuit 41 performs the processes from step S17 onwards based on the input scope information.

If the communication with the scope fails, the message "no scope" appears on the scope information display unit 20 or the monitor display 43. This makes it possible for users to know the condition of the scope mounted, or that a scope having no scope information is mounted. When the electronic scope or fiber scope mounted has no information corresponding to scope types A, B or C (step S17, NO; step S21, NO; step S25, NO), the control circuit 41 displays "incompatible scope" on the scope information display unit 20 or the monitor display 43 (step S27), and selects the maximum opening ratio of 35% (step S29). This eliminates the possibility of a rise in temperature due to an excessive amount of light. The opening ratio lower than the maximum opening ratio is also selected when it is determined that no scope is mounted, so as to decrease the amount of illumination light leaking from the light guide socket 13, if any, and reduces its ambient effects. In such cases, messages saying that an incompatible scope is mounted or that no scope is mounted is displayed (on the scope information display unit 20 or the monitor display 43) so as to inform the user.

In the second embodiment, step S62 is added before step S63, and step S64 is added after step S63. At step S62, the control circuit 41 checks whether or not the scope is detached, i.e., whether the scope lock switch 32 detects an unlocked state. If the scope is detached (step S62, YES), the control circuit 41 sets the maximum aperture opening ratio to 35%, and proceeds to step S63. If the scope is not detached (step S62, NO), the control circuit 41 simply proceeds to step S63.

According to the second embodiment, the aperture is set to the maximum aperture opening ratio of 35% if it is determined that the scope is detached in the middle of the power-ON process. This can reduce the amount of light that leaks if the scope is detached.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. An endoscope light source unit for making illumination light from a light source incident on an incident end face of a light guide connected thereto, said endoscope light source unit comprising:

an aperture device having a plurality of aperture openings of different opening ratios, for selectively positioning one of said aperture openings between said incident end face of said light guide and said light source;

a reading device for reading information on an illumination light quantity limit from a memory provided in a scope which is connected to said endoscope light source unit; and a controller for selecting an opening ratio of said aperture device in accordance with said information on said illumination light quantity limit read by said reading device, wherein said controller controls said aperture device so as not to position any of said aperture openings, which have an opening ratio higher than said selected opening ratio, between said incident end face of said light guide and said light source;

wherein said aperture device comprises a disc and drive device for rotatably driving said disc, said aperture openings of different aperture ratios being formed in said disc at equi-angular intervals thereon about a center of rotation thereof; and wherein said disc further comprises an aperture position hole for detecting an initial position of rotation of said disc.

2. The endoscope light source unit according to claim 1, wherein said information on said illumination light quantity limit comprises identification information measured and set in advance in terms of light quantity and temperature.

3. The endoscope light source unit according to claim 1, wherein said controller controls said drive device so that one of said aperture openings intersects an illumination optical path between said incident end face of said light guide and said light source.

4. The endoscope light source unit according to claim 3, wherein each of said aperture openings comprises a plurality of small holes formed in said disc at predetermined intervals; and wherein said opening ratios are determined by differing densities of said small holes.

5. The endoscope light source unit according to claim 3, wherein each of said aperture openings comprises a plurality of small holes formed in said disc at predetermined intervals; and wherein said opening ratios are determined by differing diameters of said small holes.

6. The endoscope light source unit according to claim 3, wherein each of said aperture openings comprises a plurality of small holes formed in said disc at predetermined intervals; and
wherein said opening ratios are determined by differing densities and diameters of said small holes.

7. The endoscope light source unit according to claim 3, wherein said small holes are circular in shape.

8. The endoscope light source unit according to claim 3, wherein said small holes are polygonal in shape.

9. The endoscope light source unit according to claim 3, further comprising:
an initial-position detection sensor which detects a initial position of said disc, wherein one of said plurality of aperture openings which have a smaller opening ratio than a maximum opening ratio intersects said illumination optical path between said incident end face of said light guide and said light source at said initial position;
wherein said maximum opening ratio of said aperture openings of said disc is an opening ratio which prevents an excessively large quantity of said illumination light from passing through said disc to provide a safe light quantity for any electronic scope which is connectable to said endoscope light source unit;
wherein said controller drives said drive device so as to rotate said disc so that said one of said plurality of aperture openings intersects said illumination optical path between said incident end face of said light guide and said light source.

10. The endoscope light source unit according to claim 9, wherein an aperture opening having said maximum opening ratio or said one of said aperture openings which is smaller than said maximum opening ratio, intersects said illumination optical path between said incident end face of said light guide and said light source at said initial position.

11. An endoscope light source unit for making illumination light from a light source incident on an incident end face of a light guide connected thereto, said endoscope light source unit comprising:
an aperture device having a plurality of aperture openings of different opening ratios, for selectively positioning one of said aperture openings between said incident end face of said light guide and said light source;
a reading device for reading information on an illumination light quantity limit from a memory provided in a scope which is connected to said endoscope light source unit; and
a controller for selecting an opening ratio of said aperture device in accordance with said information read by said reading device, wherein said controller controls said aperture device so as not to position any of said aperture openings, which have an opening ratio higher than said selected opening ratio, between said incident end face of said light guide and said light source,
wherein said controller selects an opening ratio lower than a maximum opening ratio of said aperture device in the case where said reading device fails to read said information on the illumination light quantity limit from said memory.

12. The endoscope light source unit according to claim 11, wherein the controller selects an opening ratio which is lower than said maximum opening ratio of said aperture device in the case where said controller determines via said reading device that no scope is connected to said endoscope light source unit.

13. The endoscope light source unit according to claim 12, further comprising a display device for displaying a result of determination of the controller.

14. The endoscope light source unit according to claim 11, wherein said controller selects an opening ratio which is lower than said maximum opening ratio of said aperture device in the case where said controller determines via said reading device that a fiber scope is connected to said endoscope light source unit.

15. The endoscope light source unit according to claim 14, further comprising a display device for displaying a result of determination of the controller.

16. The endoscope light source unit according to claim 11, wherein said information on the illumination light quantity limit comprises identification information measured and set in advance in terms of light quantity and temperature.

17. The endoscope light source unit according to claim 11, wherein said aperture device comprises:
a disc and drive device for rotatably driving said disc, said aperture openings of different aperture ratios being formed in said disc at equi-angular intervals thereon about a center of rotation thereof; and
wherein said controller drives said drive device so that one of said aperture openings intersects an illumination optical path between said incident end face of said light guide and said light source.

18. The endoscope light source unit according to claim 17, further comprising:
an initial-position detection sensor which detects a initial position of said disc, wherein one of said plurality of aperture openings which have a smaller opening ratio than a maximum opening ratio intersects said illumination optical path between said incident end face of said light guide and said light source at said initial position;
wherein said maximum opening ratio of said aperture openings of said disc is an opening ratio which prevents an excessively large quantity of said illumination light from passing through said disc to provide a safe light quantity for any electronic scope which is connectable to said endoscope light source unit;
wherein said controller drives said drive device so as to rotate said disc so that said one of said plurality of aperture openings intersects said illumination optical path between said incident end face of said light guide and said light source.

19. The endoscope light source unit according to claim 18, wherein an aperture opening having said maximum opening ratio or said one of said aperture openings which is smaller than said maximum opening ratio, intersects said illumination optical path between said incident end face of said light guide and said light source at said initial position.

20. The endoscope light source unit according to claim 17, further comprising:
a main switch for supplying power to said controller; and
a lamp switch for turning ON said light source,
wherein when said main switch is turned ON, said controller reads said information on the illumination light quantity limit, selects an opening ratio, and drives said drive device so that an aperture opening of said aperture device having the selected opening ratio intersects said illumination optical path between said incident end face of said light guide and said light source.

* * * * *